(12) United States Patent
Torii et al.

(10) Patent No.: US 6,860,602 B2
(45) Date of Patent: Mar. 1, 2005

(54) APPARATUS FOR EXAMINING AN ANTERIOR-SEGMENT OF AN EYE

(75) Inventors: Miwako Torii, Toyohashi (JP); Setsuo Saito, Aichi-gun (JP); Toshifumi Sumiya, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 66 days.

(21) Appl. No.: 10/261,602

(22) Filed: Oct. 2, 2002

(65) Prior Publication Data

US 2003/0063258 A1 Apr. 3, 2003

(30) Foreign Application Priority Data

Oct. 2, 2001 (JP) .................................... 2001-306983
Oct. 2, 2001 (JP) .................................... 2001-306984

(51) Int. Cl.$^7$ ............................................. A61B 3/10
(52) U.S. Cl. ................................................. 351/214
(58) Field of Search ............................ 351/200, 205, 351/206, 211, 212, 214, 221, 246; 382/128, 131, 154, 165; 345/418, 419, 581, 589, 619; 702/150–153, 155–158, 170, 172

(56) References Cited

U.S. PATENT DOCUMENTS

| | | | |
|---|---|---|---|
| 5,202,708 A | 4/1993 | Sasaki et al. | |
| 5,347,331 A | 9/1994 | Isogai et al. | |
| 5,512,965 A | 4/1996 | Snook | |
| 5,512,966 A | 4/1996 | Snook | |
| 5,735,283 A * | 4/1998 | Snook | ......................... 351/212 |
| 5,757,462 A | 5/1998 | Nanjo | |
| 5,864,382 A | 1/1999 | Soya et al. | |
| 6,074,063 A | 6/2000 | Hanaki | |
| 6,155,683 A | 12/2000 | Hanaki et al. | |
| 6,354,705 B1 * | 3/2002 | Hirohara et al. | ............. 351/214 |
| 6,487,432 B2 * | 11/2002 | Slack | ......................... 382/131 |

\* cited by examiner

Primary Examiner—Brian L. Casler
Assistant Examiner—John R. Sanders
(74) Attorney, Agent, or Firm—Oliff & Berridge, PLC

(57) ABSTRACT

An apparatus for examining an anterior-segment of an eye, capable of grasping each part of the anterior-segment of the eye three-dimensionally and the condition of the center of its pupil accurately. The apparatus is provided with a projection optical system for projecting slit light onto the anterior-segment, which has an optical axis of projection, an image-pickup optical system for picking up a cross-sectional image of the anterior-segment which is optical-sectioned by the projected slit light, which has an optical axis of image-pickup inclined toward the projection optical axis, and comprises an image-pickup lens and an image-pickup device arranged based on the Scheimpflug's rule, rotation means for rotating the projected slit light and the image-pickup optical system about the projection optical axis, and display means for displaying a three-dimensional image of the anterior-segment based on the cross-sectional images picked up at a plurality of angles and the image-pickup angles corresponding to the images.

16 Claims, 7 Drawing Sheets

APPARATUS FOR EXAMINING AN ANTERIOR-SEGMENT OF AN EYE

BACKGROUND OF THE INVENTION

1. Field of the Invention

The present invention relates to an apparatus for examining an anterior-segment of an eye.

2. Description of Related Art

There is an apparatus for obtaining a cross-sectional image of an anterior-segment of an eye by optical-sectioning the anterior-segment with slit light and picking up the image of the optical-sectioned anterior-segment by means of an image-pickup optical system configured based on the Scheimpflug's rule. Based on the obtained cross-sectional image, the shape of each part of the anterior-segment such as a cornea or a crystalline lens, the condition of opacity therein, and the like are examined.

One example of such apparatuses is an apparatus disclosed in U.S. Pat. No. 6,074,063 by the present applicant. This apparatus is used to obtain a retroillumination image of an anterior-segment of an eye first, and to obtain a predetermined or intended cross-sectional image of the anterior-segment based on the retroillumination image. However, it is difficult to grasp each part of the anterior-segment three-dimensionally (stereoscopically) using this apparatus. Accordingly, it is also difficult to grasp the condition of opacity three-dimensionally.

On the other hand, there is also an apparatus disclosed in U.S. Pat. No. 5,512,965. This apparatus is used to provide scanning with slit light extending in a vertical direction of an eye so that the scanning may be provided at regular intervals in a lateral direction of the eye, thereby obtaining a plurality of cross-sectional images of the anterior-segment of the eye, and obtaining the shapes of the front and rear surfaces of a cornea and the thickness of the cornea, or the condition of opacity in the cornea, based on the obtained cross-sectional images. With this apparatus, however, only a cornea may be grasped three-dimensionally. In addition, the condition of the center of a pupil (pupillary area) having a great influence on visual acuity may be grasped only as accurately as the periphery of the pupil.

SUMMARY OF THE INVENTION

The present invention has been made in view of the above-described circumstances and has an object to overcome the above problems and to provide an apparatus for examining an anterior-segment of an eye, which is capable of grasping each part of the anterior-segment of the eye three-dimensionally and the condition of the center of its pupil accurately.

To achieve the objects and in accordance with the purpose of the present invention, as embodied and broadly described herein, an apparatus for examining an anterior-segment of an eye is provided with the following: a) a projection optical system for projecting slit light onto the anterior-segment, the projection optical system having an optical axis of projection; b) an image-pickup optical system for picking up a cross-sectional image of the anterior-segment optical-sectioned by the projected slit light, the image-pickup optical system having an optical axis of image-pickup inclined toward the projection optical axis and comprising an image-pickup lens and an image-pickup device both of which are arranged based on the Scheimpflug's rule; c) rotation means for rotating the projected slit light and the image-pickup optical system about the projection optical axis; and d) display means for displaying a three-dimensional image of the anterior-segment based on the cross-sectional images picked up at a plurality of angles and the image-pickup angles corresponding to the images.

In another aspect of the present invention, an apparatus for examining an anterior-segment of an eye is provided with the following: a) a projection optical system for projecting slit light onto the anterior-segment, the projection optical system having an optical axis of projection; b) an image-pickup optical system for picking up a cross-sectional image of the anterior-segment which is optical-sectioned by the projected slit light, the image-pickup optical system having an optical axis of image-pickup inclined toward the projection optical axis and comprising an image-pickup lens and an image-pickup device both of which are arranged based on the Scheimpflug's rule; c) rotation means for rotating the projected slit light and the image-pickup optical system about the projection optical axis; d) analysis means for obtaining a luminance distribution in each image and a three-dimensional position of the luminance distribution, based on the cross-sectional images picked up at a plurality of angles and the image-pickup angles corresponding to the images; and e) display means for displaying a portion of the obtained luminance distribution falling within a range of intended luminance levels in relation to the three-dimensional position.

Yet, in another aspect of the present invention, an apparatus for examining an anterior-segment of an eye is provided with the following: a) a projection optical system for projecting slit light onto the anterior-segment, the projection optical system having an optical axis of projection; b) an image-pickup optical system for picking up a cross-sectional image of the anterior-segment which is optical-sectioned by the projected slit light, the image-pickup optical system having an optical axis of image-pickup inclined toward the projection optical axis and comprising an image-pickup lens and an image-pickup device both of which are arranged based on the Scheimpflug's rule; c) rotation means for rotating the projected slit light and the image-pickup optical system about the projection optical axis; and d) analysis means for obtaining a three-dimensional position of an intended part of the anterior-segment to obtain a three-dimensional shape thereof, based on the cross-sectional images picked up at a plurality of angles and the image-pickup angles corresponding to the images.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
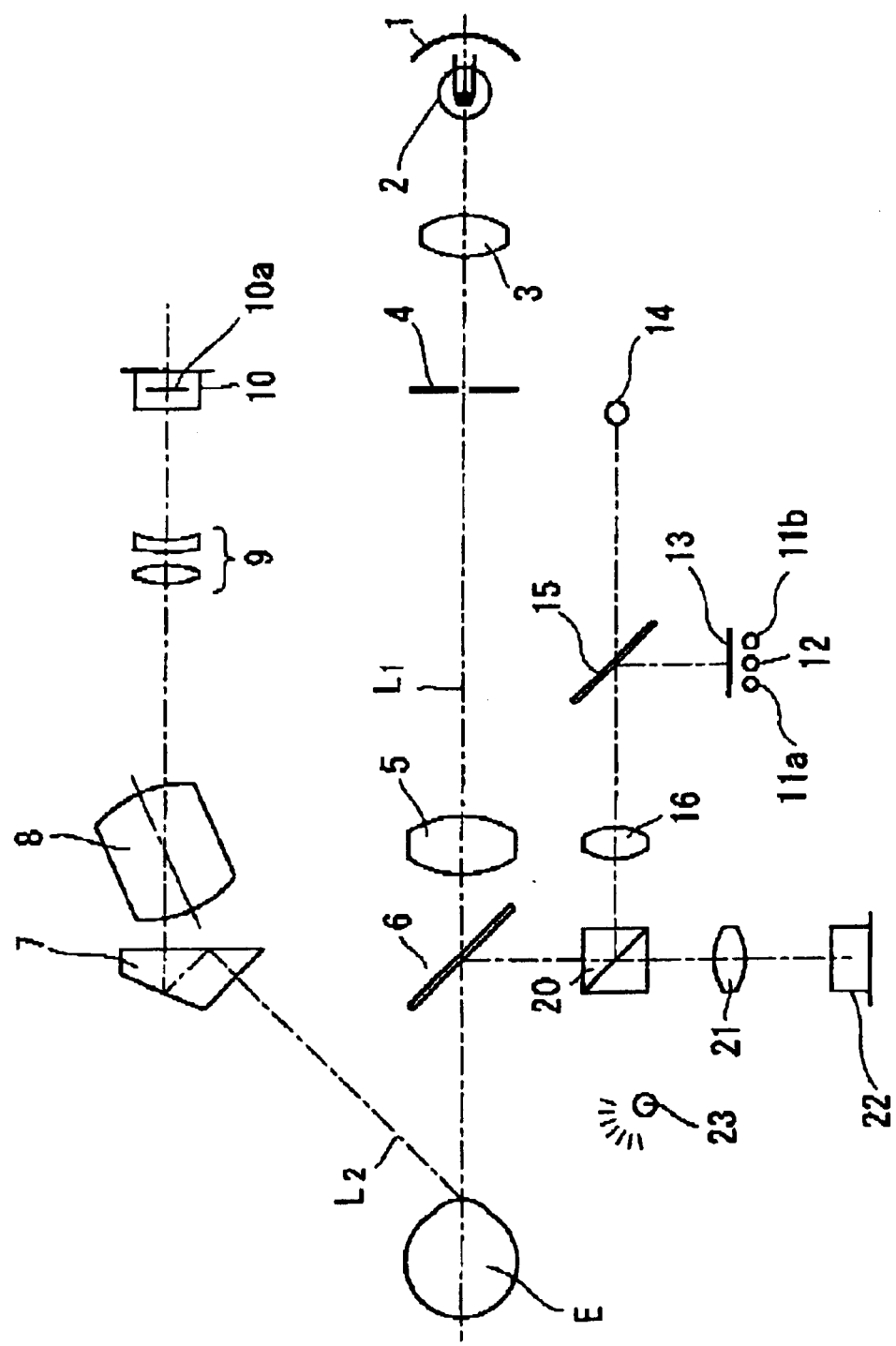
FIG. 1 shows a schematic configuration of an optical system in an apparatus according to the present invention.

A detailed description of one preferred embodiment of an apparatus for examining an anterior-segment of an eye embodying the present invention will now be given referring to the accompanying drawings. FIG. 1 shows a schematic configuration of an optical system in the apparatus consistent with the present invention. The optical system is roughly constituted of a slit-light projecting optical system, an image-pickup optical system for a cross-sectional image of an anterior-segment of an eye, an alignment-target projecting optical system, a fixation-target presenting optical system, and an image-pickup optical system for a front image of an anterior-segment of an eye.

<Slit-Light Projecting Optical System>

Reference numeral 1 indicates a reflecting mirror, 2 is a halogen lamp as a light source for image-pickup, 3 is a condenser lens, 4 is a slit-aperture diaphragm, 5 is a projecting lens, and 6 is a dichroic mirror disposed slantingly on an optical axis L1 of the slit-light projecting optical system. The dichroic mirror 6 has a property of transmitting most of visible light but reflecting part of the visible light and all of infrared light (near-infrared light). The light source for image-pickup is not limited to a halogen lamp, and may be any of a wide variety of visible white light sources including a strobe lamp, an LED and the like. Further, an infrared (near-infrared) light source may be used as well.

Visible white light emitted from the lamp 2 converges by the lens 3 to illuminate the diaphragm 4. The light limited in narrow slit shape by the diaphragm 4 passes through the lens 5 and the dichroic mirror 6 to be projected onto an eye E to be examined. Optic media (a cornea, an anterior chamber, a crystalline lens, and the like) of an anterior segment of the eye E are illuminated and optical-sectioned by the visible white light.

<Image-Pickup Optical System for a Cross-Sectional Image of an Anterior-Segment of an Eye>

Reference numeral 7 indicates a deflection-angle prism, 8 is an image-pickup lens, 9 is an anamorphic lens for correcting image distortion, and 10 is a highly sensitive CCD camera for picking up a cross-sectional image. An optical axis L2 of the image-pickup optical system for a cross-sectional image is inclined at an angle of 45 degrees toward the optical axis L1. The lens 8 is inclined at a certain angle toward an image-pickup optical axis of which orientation is changed by the prism 7, thereby satisfying the Scheimpflug's rule. That is, when the prism 7 is removed, the lens 8 is arranged so that an extension of an optical cross section of the anterior-segment of the eye E and an extension of an imaging surface 10a of the camera 10 may intersect on an extension of a main plane of the lens S. This optical arrangement allows the sectional image formed on the imaging surface 10a of the camera 20 to have a focal depth at which the approximately entire image is in focus.

<Alignment-Target Projecting Optical System>

Reference numeral 14 indicates a near-infrared light source for alignment, 15 is a dichroic mirror having a property of reflecting most of infrared light (near-infrared light) but transmitting part of the infrared light (near-infrared light), and reflecting all of visible light, and 16 is a projecting lens. Part of near-infrared light emitted from the light source 14 is transmitted through the dichroic mirror 15, is made to be a parallel light bundle by the projecting lens 16, and is partially reflected by a half mirror 20. Then, this light is reflected by the dichroic mirror 6, and proceeds along the optical axis L1 toward the eye E, thereby forming an image of the light source 13 inside the eye at a distance of half a radius of corneal curvature from a corneal vertex.

<Fixation-Target Presenting Optical System>

Reference numeral 11a and 11b indicate light sources for eye fixation. In the present embodiment, each of right and left eyes is provided with one each of the light sources for eye fixation so that a geometric axis (an optical axis) of the eye E may coincide with the optical axis L1 at the time of image-pickup, whereby an image picked up from a nose side and that from an ear side are mirror images of each other (see Japanese Patent Application Unexamined Publication No Hei 04-96730 (U.S. Pat. No. 5,202,708)). A light source 12 emits near-infrared light for picking up a retroillumination image. A target plate 13 includes pinholes at positions corresponding to the light sources 11a, 11b and 12. Visible light emitted from the light sources 11a and 11b illuminates the target plate 13. The light having passed through the aperture of the target plate 13 is reflected by the dichroic mirror 15, and proceeds toward the eye E via the lens 16, the half mirror 20, and the dichroic mirror 6.

<Image-Pickup Optical System for a Front Image of an Anterior-Segment of an Eye>

Reference numeral 21 indicates an image-pickup lens, and 22 is a CCD camera for picking up a front image with a sensitivity to the infrared region (near-infrared region). An illumination light source 23 for an anterior-segment of an eye emits near-infrared light. An image of the anterior-segment of the eye E illuminated by the light source 23 is formed on an imaging surface of the camera 22 via the dichroic mirror 6, the half mirror 20 and the lens 21. The light from the alignment-target projecting optical system is reflected by the cornea, and forms an image on the imaging surface of the camera 22 through the same optical path.

Figure 2:
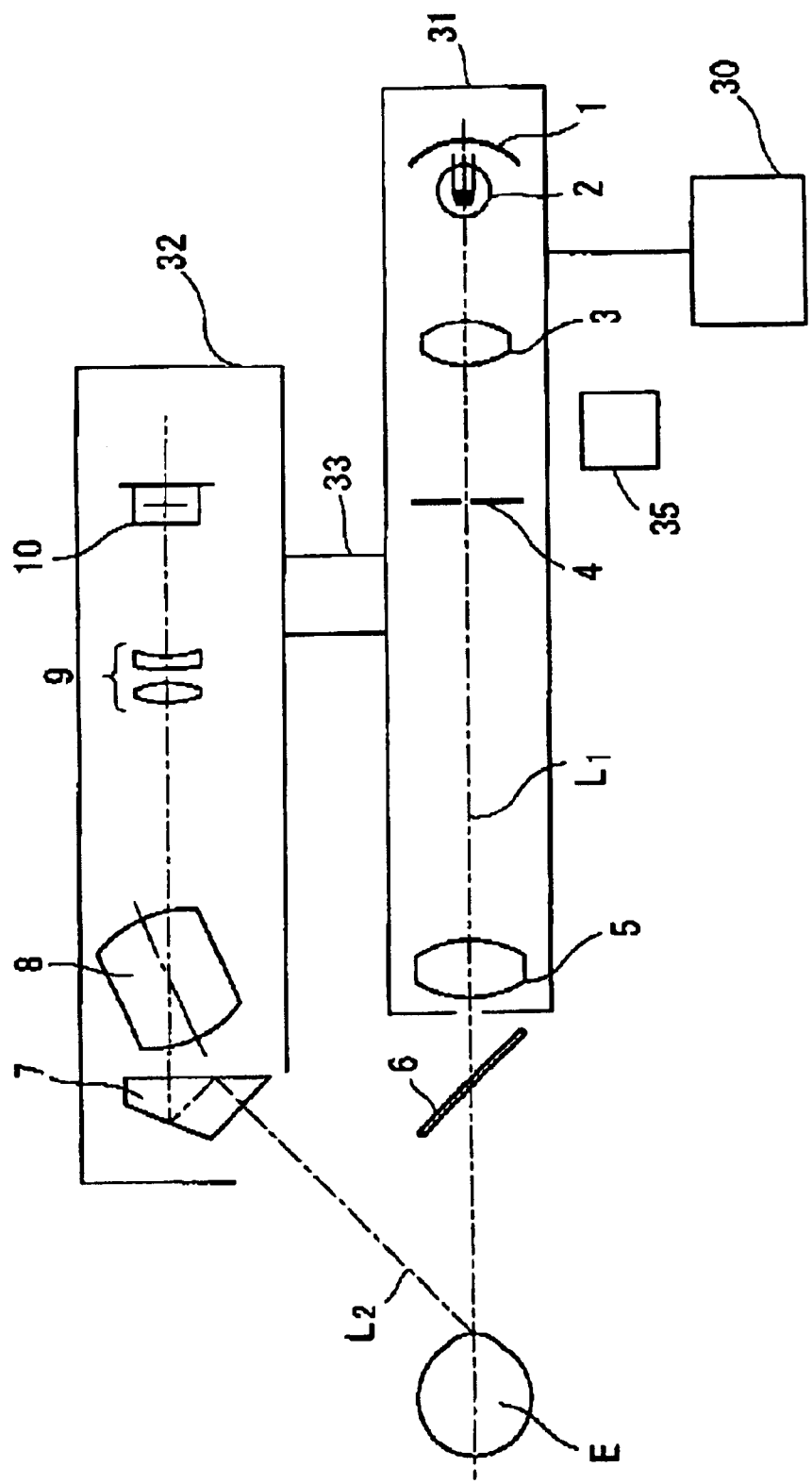
FIG. 2 shows a schematic configuration of a rotation mechanism for the optical system.

FIG. 2 shows a schematic configuration of a rotation mechanism for the optical system. A holding unit 31 holds the elements of the slit-light projecting optical system including the reflecting mirror 1 to the lens 5. The holding unit 31 is held rotatably about the optical axis L1 inside the housing of the main body of the apparatus, and is rotated by a pulse motor 30 via a rotation-conveying element such as a gear. A holding unit 32 holds the elements of the image-pickup optical system for a cross-sectional image, including the prism 7 to the camera 10. The holding unit 32 is fastened to the holding unit 31 with a fastening element 33. These structures allow the slit light projected onto the eye E and the cross-sectional-image-pickup optical system to be rotated about the optical axis L1. A sensor 35 detects a position of an initial rotation of the holding unit 31 (or the holding unit 32).

Figure 3:
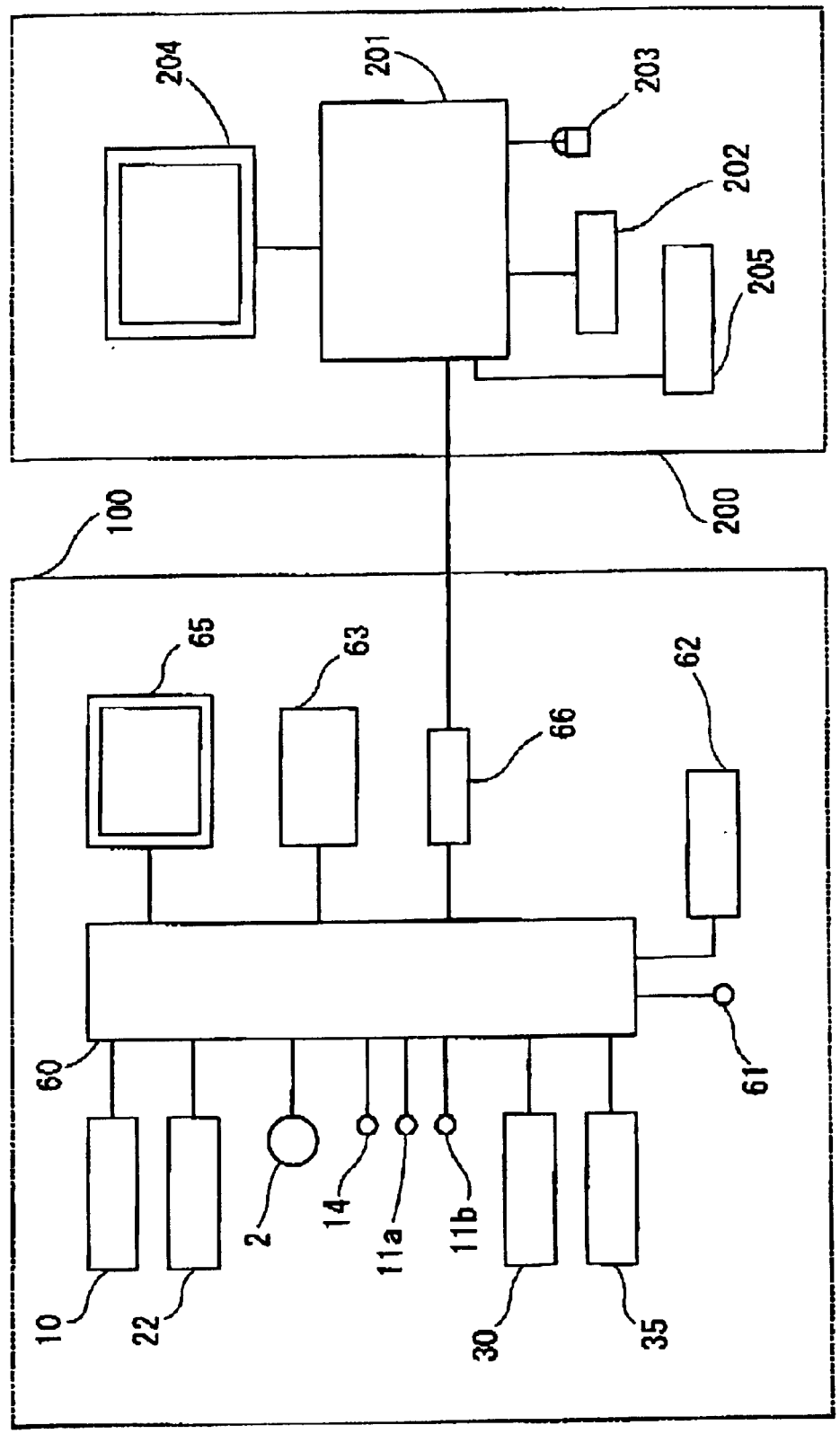
FIG. 3 shows a control system in the present apparatus.

FIG. 3 shows a schematic configuration of a control system of the present apparatus. The aforementioned optical system and rotation mechanism are placed in an image-pickup unit 100. A control part 60 is connected with the cameras 10 and 22, the light sources such as the lamp 2, the motor 30, the sensor 35, an image-pickup switch 61, a control panel 62 with a variety of switches, a memory 63 for storing an image, a display 65 for displaying an image, an output part 66 for outputting an image, and the like, each of which is controlled by the control part 60.

An analysis unit 200 includes a computer part 201 for processing and analyzing an image from the image-pickup unit 100. The computer part 201 has a memory for storing an image and an analysis program. Connected to the computer 201 are a keyboard 202, a mouse 203, a color display 204, a printer 205, and the like, each of which is controlled by the computer 201.

The operation of the apparatus configured as above will now be explained. The eye E is placed at a predetermined position. The control part 60 lights up the light source 11a or 11b based on a signal specifying the right or left eye (and the eye E gazes at that light source 11a or 11b). A front image of the eye E is obtained by the camera 22, and is then displayed on the display 65. An examiner operates an joystick or the like (not shown) to move the image-pickup unit 100 vertically or laterally for alignment with the eye E, thereby creating predetermined relations between an image of the alignment target (the image of the light source 14 and an image of a reticle which is electrically formed (or may be optically formed), both images being displayed on the display 65. Thus, the optical axis of the optical system is aligned with that of the eye E. In addition, the image-pickup unit 100 is moved back and forth to adjust a working distance so that the image of the alignment target may be the smallest and clearest.

Upon completion of the alignment, the examiner operates the switch 61 to start image pickup. Based on a signal from the switch 61, the control part 60 lights up the lamp 2 and drives the motor 30 to rotate the holding unit 31 (the slit-light projecting optical system) and the holding unit 32 (the cross-sectional-image-pickup optical system) about the optical axis L1. When the lamp 2 is lit up, the anterior-segment of the eye E is optical-sectioned by slit light. The light scattering from the optical-sectioned anterior-segment forms an image on the imaging surface 10a of the camera 10. At this time, the control part 60 causes the camera 10 to synchronize to the number of pulses from the motor 30; the camera 10 thereby obtains the image at each predetermined angle of rotation; and the control part 60 then stores the obtained image in the memory 63. Also, each angle at which the image is picked up is stored associated with the corresponding image. While the images are being picked up during rotation, the intensity of light from the lamp 2 is controlled to be constant.

Since a rotation half around provides images for all around, it is preferable that the number of the images be at least eighteen (when the rotation is made in steps of 10 degrees), or more preferably at least thirty six (the rotation angle of every 5 degrees). In this embodiment, to perform an analysis as accurately as possible, if the width of the slit light is 80 µm, eighty images are picked up at each rotation angle of 2.25 degrees, and are then stored automatically in the memory 63. It should be noted that the rotation angle may be fixed, but may also be adjusted arbitrarily.

Before picking up an image, the holding units 31 and 32 (the slit-light projecting optical system and the cross-sectional-image-pickup optical system) are placed at the initial angle. The sensor 35 detects whether they are at the initial angle or not. The positioning to the initial angle is conducted on the actuation of the apparatus or at the press of a reset switch on the control panel 62. The holding units 31 and 32 are also positioned at the initial angle at the completion of the image-pickup.

Once all the images have been obtained, an image transfer switch on the control panel 62 is pressed to output to the computer part 201 all the images and their corresponding image-pickup angles stored in the memory 63. In the computer part 201, the analysis program is executed to construct a three-dimensional image based on all the images and image-pickup angles.

Figure 4:
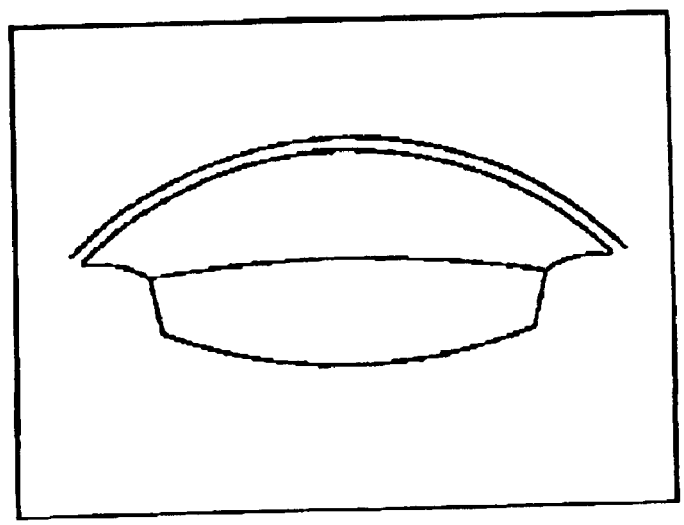
FIG. 4 shows an example of display of a cross-sectional image of an anterior-segment of an eye obtained through image-pickup.

The construction of a three-dimensional image will now be explained. As shown in FIG. 1, in the optical system in the present apparatus, a plane of an object is inclined at a 45-degree angle toward the image-pickup optical axis, and the plane of the image-pickup lens 8 is inclined at a specified angle toward the image-pickup optical axis, thereby meeting the Scheimpflug's rule. However, such an arrangement distorts the length-to-width ratio of an image on the imaging surface. Such image distortion owing to the Scheimpflug's rule may be corrected by the placement of the anamorphic lens 9. FIG. 4 shows an example of display of an anterior-segment cross-sectional image obtained through the image-pickup. Incidentally, the image distortion due to the Scheimpflug's rule may also be corrected by image processing.

In addition, the light scattering from the optical-sectioned anterior-segment passes through not only the cross-sectional-image-pickup optical system, but part of that light also passes through the inside of the eye (the optic media of the anterior-segment of the eye). Consequently, the light is refracted inside the eye, thus obtaining a distorted image. To obtain the position of each part inside the eye, it is preferable to compensate for an influence from the refraction caused by the optic media of the anterior-segment. The distorted image is corrected utilizing ray tracing.

The ray tracing may be performed using Feder's general ray tracing formula. For the ray tracing, the data concerning an apparent position of each part in a cross-sectional image and the refractive index of each part are provided (general known values are used). And, in the Feder's formula, the coordinates where a ray of light passes through and the direction of the ray are expressed by direction cosine, whereby the ray is traced.

The computer 201 is used to perform the ray tracing on the respective parts (the positions of the front and rear surfaces of a cornea, the front and rear surfaces of a crystalline lens, and the like) in each image so as to correct their apparent positions. Then, based on the positions obtained by the correction and the image-pickup angles, the computer 201 calculates three-dimensional positions from all the images. The part of which image has not been obtained is interpolated from its neighboring images. Thus, a three-dimensional image of the anterior-segment is constructed. In addition, a three-dimensional position corresponding to a luminance value of each part is obtained.

Figure 5:
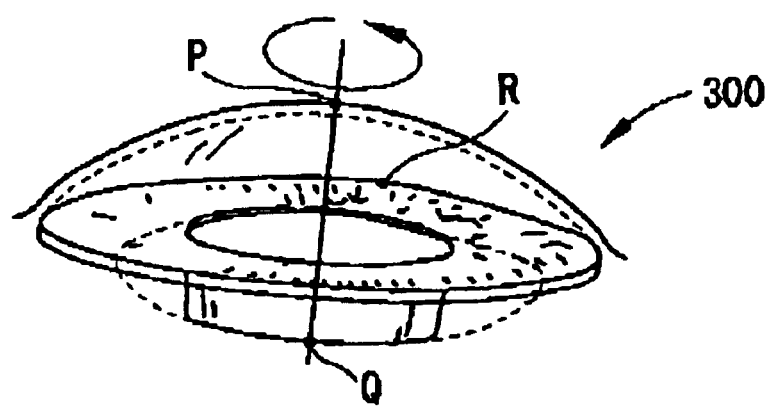
FIG. 5 shows an example of display of a three-dimensionally constructed image of the anterior-segment.

On the display 204, as shown in FIG. 5, a constructed three-dimensional image 300 of the anterior-segment is displayed graphically. The three-dimensional image 300 of the anterior-segment may be displayed in such a manner that it is viewed from various directions (from various angles) through the operation of the mouse 203 or the like.

Figure 6:
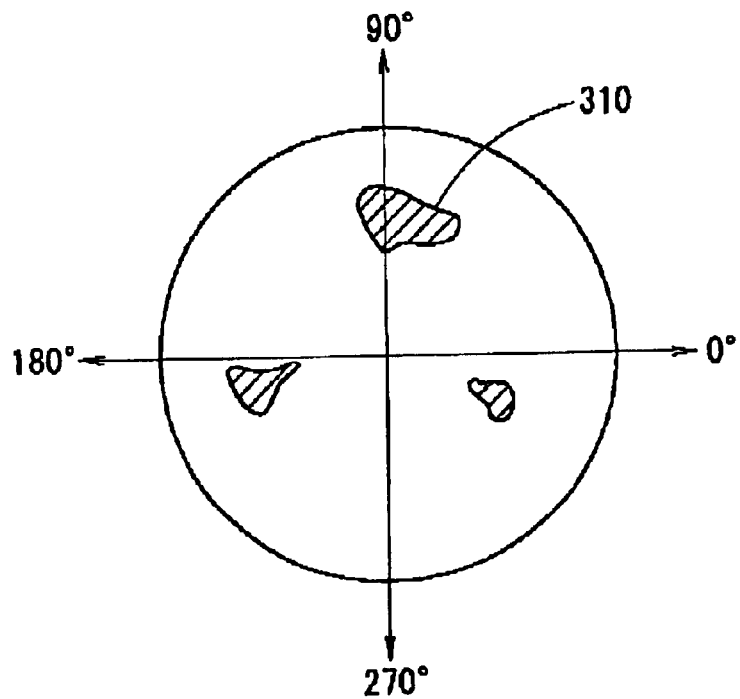
FIG. 6 shows an example of display of an image illustrating the condition of an opacity part viewed from the front side.

The analysis of opacity (luminance) will now be explained. By way of example, a description will be given to the case of analyzing the condition of opacity in a crystalline lens. The obtained cross-sectional image is formed by the light scattering from the anterior-segment which is optical-sectioned by the slit light, and the luminance of the image increases with the degree of opacity. The density value of opacity may therefore be quantified based on the luminance. For example, it maybe expressed in 256 levels ranging from 0 to 255 (unit; cct). When an opacity analysis mode is selected, a distribution of the density values is presented as a bar graph on the display 204. When the examiner specifies an arbitrary density value, one or more parts having density values greater than the specified value (one or more parts having higher degrees of opacity) is extracted and displayed three-dimensionally on the display 204. FIG. 6 shows an example of display of the crystalline lens viewed from the front side, where diagonally shaded areas 310 signify opacity parts. The opacity parts 310 may also be displayed in such a manner that they are viewed from various directions (from various angles) through the operation of the mouse 203 or the like. This makes it easier to visually grasp the degree of opacity and the positions of the opacity parts. When viewed from the front or retina side, the opacity parts and the degree of opacity may be observed more precisely than when displayed in the form of a retroillumination image. The volume of the extracted opacity parts 310 is calculated, and a result of the calculation is displayed.

Figure 7:
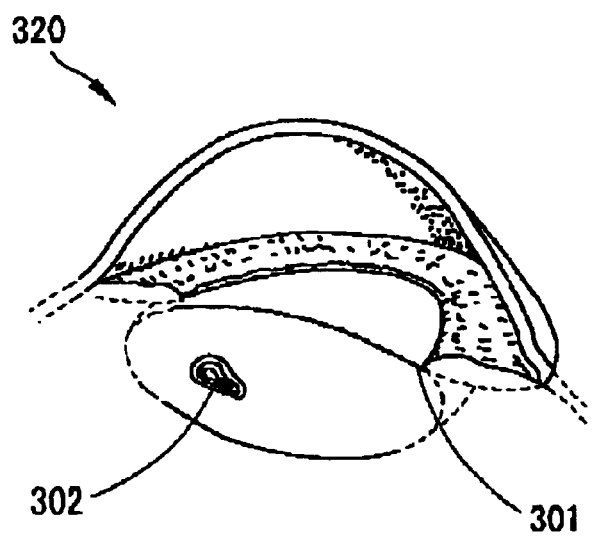
FIG. 7 shows an example of display of the three-dimensional image of the anterior-segment including a cross section.

In addition, the opacity analysis may be conducted with respect to any given cross section (plane). In the display shown in FIG. 5, the examiner specifies three points P, Q, and R using the mouse 203 or the like to determine a cross section to be analyzed on the three-dimensional image 300 of the anterior-segment. Alternatively, the examiner may also determine the cross section to be analyzed in the following manner: first he specifies two points P and Q to form a straight line included in the cross section to be analyzed; then identifies the cross section to be analyzed while viewing the image as rotated about the straight line; and finally specifies a point R. This may also be done in the display form shown in FIG. 6. On the display 204, a three-dimensional image 320, including a cross section 301 obtained by sectioning the three-dimensional image 300, is displayed as shown in FIG. 7. In the three-dimensional image 320, a color distribution associated with the density values is displayed as a color map. In FIG. 7, the area indicated by Reference numeral 302 is a color-mapped opacity part. The color map is created by, for example, classifying the density values into four levels and color-coding them in four colors associated with those levels. Moreover, when any point on the opacity part 302 shown in FIG. 7 is selected using the mouse 203 or the like, the density value for the selected point is displayed. Thus, displaying a three-dimensional image including a cross section makes it easier to grasp the positional relations among opacity parts.

In this connection, only a specified cross section may be displayed two-dimensionally. In this case, as for a section crossing the optical axis, a cross-sectional image may be picked up and displayed, and an opacity part under color mapping may be synthetically superimposed on the displayed cross-sectional image. As a matter of course, only such a cross-sectional image as shown in FIG. 4 may be displayed selectively by specifying a particular image-pickup angle.

Further, on any specified cross-section, the density values may be separated into several grades, and the specified cross section (and a cross section as an enlarged view of the specified part as well) may be divided into a number of areas in matrix form, in which the density value graded for each area may be shown.

As described above, the opacity in a crystalline lens has been taken as an example, but the same steps may be performed to analyze the opacity in a posterior capsule or other parts of the anterior-segment of an eye. In addition, in a case where the analysis of opacity does not necessarily require great accuracy in constructing a three-dimensional image, that image may be constructed based on the data about even the apparent positions.

Figure 8:
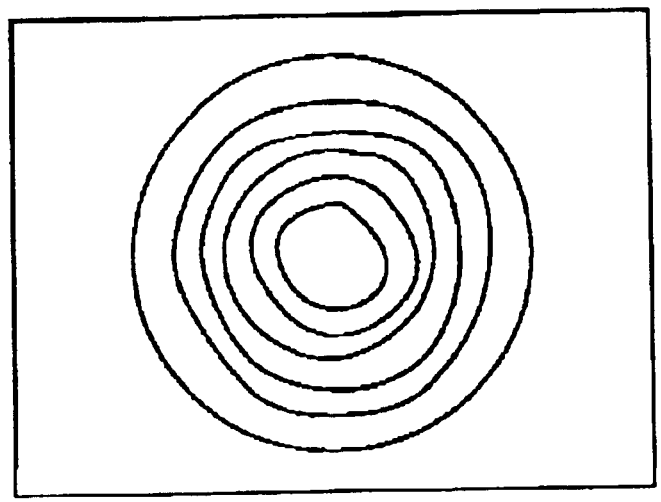
FIG. 8 shows an example of color-map display of a result of shape analysis of the front surface of a crystalline lens.

Next, the analysis of shape will now be explained. When a shape analysis mode is selected, the result of constructing a three-dimensional image of the anterior-segment may be utilized to analyze (measure) the shape of each part, on a piecemeal basis, including curvature distributions of the front and rear surfaces of a cornea, a thickness distribution of the cornea, curvature distributions of the front and rear surfaces of a crystalline lens, a thickness distribution of the crystalline lens, a depth distribution of ah anterior chamber, and the like. FIG. 8 shows an example of display of a result of the analysis, which is a color map display of the analytical result of the front surface shape of a crystalline lens. Similarly, the shapes of other parts may also be displayed in color-map form.

Figure 9:
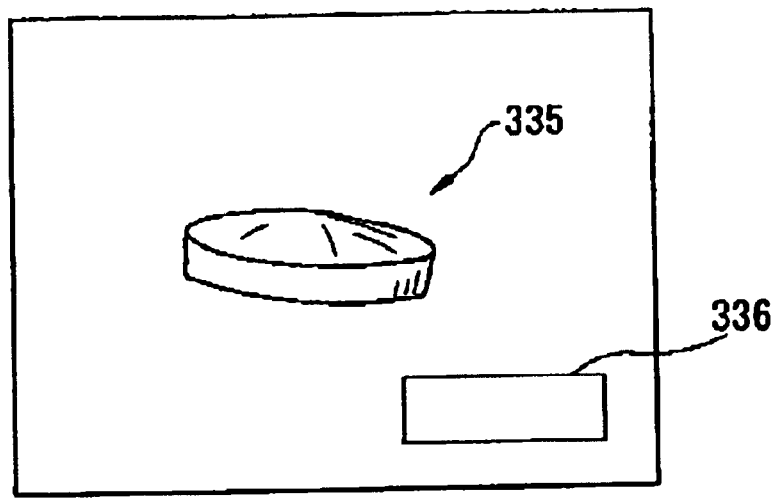
FIG. 9 shows an example of three-dimensional graphic display of the result of the shape analysis of the crystalline lens.

In addition, in the shape analysis mode, the three-dimensional shape of each part may be individually displayed in graphics. FIG. 9 shows an example of graphical display of only a crystalline lens as a three-dimensional image 335. In such display, the crystalline lens may be displayed in such a manner that it is viewed from various directions (from various angles) through the operation of the mouse 203 or the like. Similarly, an anterior chamber or a cornea may also be displayed in three-dimensional graphics. The volume of each part of the anterior-segment may be obtained based on its three-dimensional shape, and the obtained volume is numerically displayed on a display part 336. Of course, the volume of any specified region (which may be specified using the mouse 203 or the like) may be obtained as well.

Figure 10:
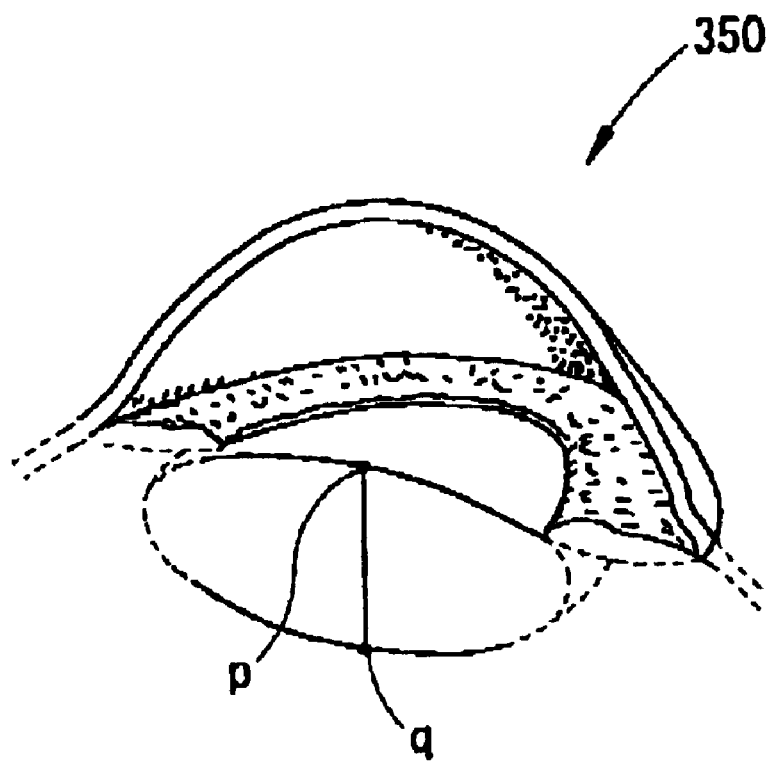
FIG. 10 shows an example of display of the result of the shape analysis as the three-dimensional image including the cross section.

Further, when the three points P, Q and R are specified on the three-dimensional image 300 of the anterior-segment shown in FIG. 5 using the mouse 203 or the like to determine a cross section to be analyzed, a three-dimensional image 350 including the cross section is displayed as shown in FIG. 10. Furthermore, on that cross section, once the points intended for measurement, for example, a starting point p and an endpoint q on the part of which measurement is desired, have been determined using the mouse 203 or the like, the measurement is taken between the two points, and the measurement result is displayed numerically. Also, a radius of curvature of a cornea or a crystalline lens may be displayed numerically as well by specifying arbitrary points on the cross section of the three-dimensional image 350. This may also be done in a like manner on the three-dimensional image 335 shown in FIG. 9.

The above-described analysis of shape is based on an anterior-segment cross-sectional image that is picked up while the slit light and the image-pickup optical system for a cross-sectional image are rotated about the optical axis (visual axis) of the eye. Therefore, the center of a pupil (pupillary area) having an intimate bearing on visual acuity may be analyzed more accurately compared with in a case where the analysis of shape is based on an anterior-segment cross-sectional image that is picked up while the slit light is translated (scanned). In addition, because of relying on the Scheimpflug's rule, a clear image covering the front surface of a cornea through the rear surface of a crystalline lens may be obtained, thereby improving accuracy in constructing a three-dimensional image.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for examining an anterior-segment of an eye, the apparatus comprising:
   a projection optical system for projecting slit light onto an eye to be examined from the front, having an optical axis of projection;
   an image-pickup optical system for picking up a cross-sectional image of the anterior-segment which is optical-sectioned by the projected slit light, having an optical axis of image-pickup inclined toward the projection optical axis, and comprising an image-pickup lens arranged based on the Scheimpflug's rule and an image-pickup device;
   a photographing sectional angle rotation unit which rotates a direction of the slit light about the projection optical axis and rotates the image-pickup optical system about the projection optical axis in correspondence with the rotation of the slit light;
   analysis means for constructing a three-dimensional image of the anterior-segment based on a number of the cross-sectional images of the anterior-segment picked up while changing the photographing sectional angle; and
   display means, including specifying means for specifying a display method, for rotatably displaying the constructed three-dimensional image of the anterior-segmentor displaying the three-dimensional image of the anterior-segment viewed from a different direction, according to the specified display method.

2. The apparatus according to claim 1, wherein the analysis means constructs the three-dimensional image of the anterior-segment ranging from a front surface of a cornea to at least a front surface of a crystalline lens.

3. The apparatus according to claim 1, further comprising specifying means for specifying at least three points intended on the displayed three-dimensional image,
   wherein the analysis mean constructs an image of a plane including the specified points.

4. The apparatus according to claim 1, wherein the analysis means obtains a luminance distribution in each cross-sectional image and a three-dimensional position of each luminance distribution, based on the cross-sectional images, and
   the display means three-dimensionally displays a portion of the obtained luminance distribution falling within a range of intended luminance levels.

5. The apparatus according to claim 4, further comprising specifying means for specifying at least three points intended on the three-dimensionally displayed luminance distribution,
   wherein the display means displays a portion of the luminance distribution of a plane including the specified points.

6. The apparatus according to claim 4, wherein the display means displays the portion of the luminance distribution within the range of the intended luminance levels using color-coding into predetermined levels.

7. The apparatus according to claim 4, wherein the analysis means obtains a volume of the portion of the luminance distribution within the range of the intended luminance levels.

8. The apparatus according to claim 4, wherein the analysis means includes:
   means for correcting image distortion owing to the Scheimpflug's rule; and
   means for correcting image distortion owing to refraction caused by optic media of the anterior-segment.

9. The apparatus according to claim 1, wherein the analysis means obtains a three-dimensional position of an intended part of the anterior-segment to obtain a three-dimensional shape thereof, based on the cross-sectional images, and
   the display means displays the obtained three-dimensional shape.

10. The apparatus according to claim 9, wherein the analysis means three-dimensionally obtains at least one of a shape of a front surface of a cornea, a shape of a rear surface of the cornea, a thickness of the cornea, a shape of a front surface of a crystalline lens, a shape of a rear surface of the crystalline lens, and a thickness of the crystalline lens.

11. The apparatus according to claim 9, wherein the analysis means obtains a volume of the obtained three-dimensional shape.

12. The apparatus according to claim 9, further comprising specifying means for specifying at least three points intended on the displayed three-dimensional shape, wherein:
   the analysis means obtains a shape of a plane including the specified points, and
   the display means displays the obtained shape of the plane.

13. The apparatus according to claim 12, wherein
   the specifying means specifies at least two points intended on the displayed shape of the plane, and
   the analysis means obtains a size based on the specified points.

14. The apparatus according to claim 1, wherein the analysis means includes:
   means for correcting image distortion owing to the Scheimpflug's rule; and
   means for correcting image distortion owing to refraction caused by optic media of the anterior-segment.

15. An apparatus for examining an anterior-segment of an eye, the apparatus comprising:
   a projection optical system for projecting slit light onto an eye to be examined from the front, having an optical axis of projection;
   an image-pickup optical system for picking up a cross-sectional image of the anterior-segment which is optical-sectioned by the projected slit light, having an optical axis of image-pickup inclined toward the projection optical axis, and comprising an image-pickup lens arranged based on the Scheimpflug's rule and an image-pickup device;
   a photographing sectional angle rotation unit which rotates a direction of the slit light about the projection optical axis and rotates the image-pickup optical system about the projection optical axis in correspondence with the rotation of the slit light;
   analysis means constructing a three-dimensional image of the anterior-segment, including opacity information based on luminance information, based on a number of the cross-sectional images of the anterior-segment picked up while changing the photographing sectional angles; and
   display means for displaying the constructed three-dimensional image of the anterior-segment, the display means including specifying means for specifying a section to be analyzed with respect to the displayed three-dimensional image and displaying the three-dimensional image sectioned at the specified section.

16. The apparatus according to claim 15, wherein the display means three-dimensionally displays an opacity portion.

* * * * *